(12) United States Patent
Carroll et al.

(10) Patent No.: US 6,484,050 B1
(45) Date of Patent: Nov. 19, 2002

(54) MINIMALLY INVASIVE SURGICAL INSTRUMENT FOR TISSUE IDENTIFICATION, DISLODGMENT AND RETRIEVAL AND METHODS OF USE

(75) Inventors: Robert G. Carroll, Largo, FL (US); Robin A. Wise, Jr., Morgan Hill, CA (US)

(73) Assignee: Care Wise Medical Products Corporation, Morgan Hill, CA (US)

( * ) Notice: Subject to any disclaimer, the term of this patent is extended or adjusted under 35 U.S.C. 154(b) by 0 days.

(21) Appl. No.: 09/201,289

(22) Filed: Nov. 30, 1998

Related U.S. Application Data

(63) Continuation-in-part of application No. 08/972,598, filed on Nov. 18, 1997, now Pat. No. 5,961,458.

(51) Int. Cl.$^7$ ................................. A61B 6/00
(52) U.S. Cl. ...................... 600/436; 600/562; 250/362; 604/27; 604/28; 604/96.01
(58) Field of Search ................ 600/436, 431, 600/204, 207, 562; 606/190, 192, 194, 186, 167, 185; 604/96.01, 27, 103.1, 28, 48; 250/370.12, 362, 363.02, 336.1

(56) References Cited

U.S. PATENT DOCUMENTS

| | | |
|---|---|---|
| 4,801,803 A | 1/1989 | Denen et al. |
| 4,959,547 A | 9/1990 | Carroll et al. |
| 5,014,708 A | 5/1991 | Ishihara et al. |
| 5,036,210 A | 7/1991 | Goodman |
| 5,108,406 A | 4/1992 | Lee .......................... 606/106 |
| 5,119,818 A | 6/1992 | Carroll et al. |
| 5,170,055 A | 12/1992 | Carroll et al. |
| 5,429,133 A | 7/1995 | Thurston et al. |
| 5,846,513 A | * 12/1998 | Carroll et al. ............... 600/436 |
| 5,982,838 A | * 11/1999 | Vourvopoulos ........ 250/390.04 |
| 6,135,955 A | * 10/2000 | Madden et al. ............. 600/436 |

FOREIGN PATENT DOCUMENTS

| | | |
|---|---|---|
| WO | WO 94/03108 | 2/1994 |
| WO | WO 97/42524 | 11/1997 |
| WO | WO 99/25248 | 5/1999 |

OTHER PUBLICATIONS

Research publication by Entine G, et al.: "Survey of CDTE Nuclear Detector Applications", Nuclear Instruments & Methods In Physics Research, Section A: Accelerators, Spectrometers, Detectors and Associated Equipment, NL, North–Holland Publishing Company, Amsterdam, vol. A283, No. 2, Nov. 1, 1989, pp. 282–290, XP000072534, ISSN:0168–9002, pp. 282–284.

\* cited by examiner

*Primary Examiner*—Ruth S. Smith
(74) *Attorney, Agent, or Firm*—Caesar, Rivise, Bernstein, Cohen & Pokotilow, Ltd.

(57) ABSTRACT

A probe or sheath for use on a probe for detecting and removing radioactively tagged tissue, e.g., a sentinel lymph node, within the body of a living being. The probe or sheath and probe is arranged to be inserted through a small percutaneous portal into the patient's body and is movable to various positions adjacent the tagged tissue to detect the presence of radiation therefrom so that it can be positioned immediately adjacent that tissue to ensnare or trap that tissue. The probe or sheath and probe can then be removed from the being's body, carrying the tagged tissue with it. The probe may be constructed to make use of a scintillation crystal, a collimator, adjustable or fixed, and a backshielding lightpipe. A blunt dissecting device is provided as part of the sheath or as part of the probe itself to aid in separating the tagged tissue from adjacent tissue without injury to the adjacent tissue. The probe may be a fully integrated, self-powered unit.

62 Claims, 6 Drawing Sheets

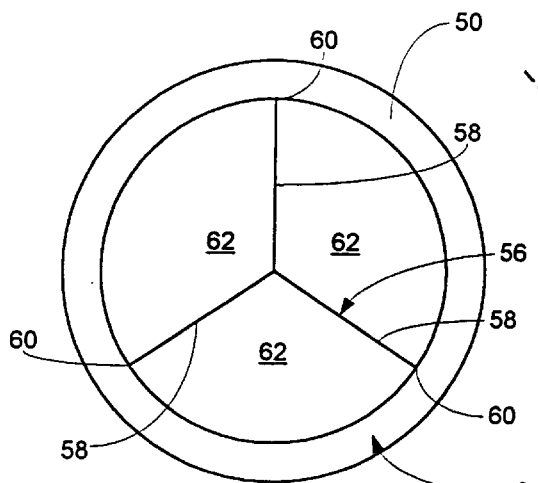
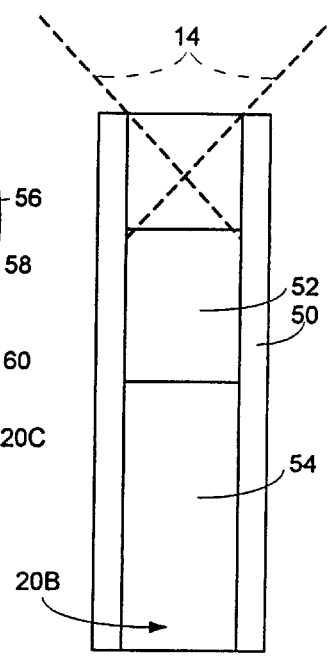
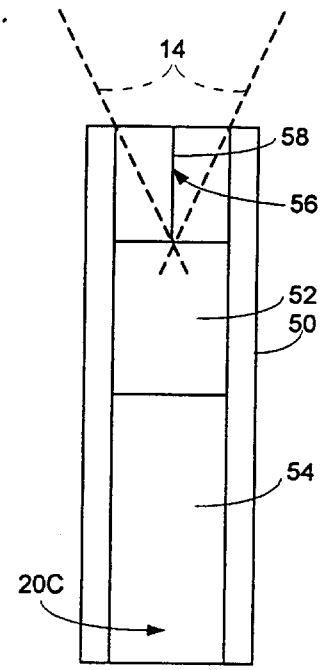
Fig. 8    Fig. 6    Fig. 7
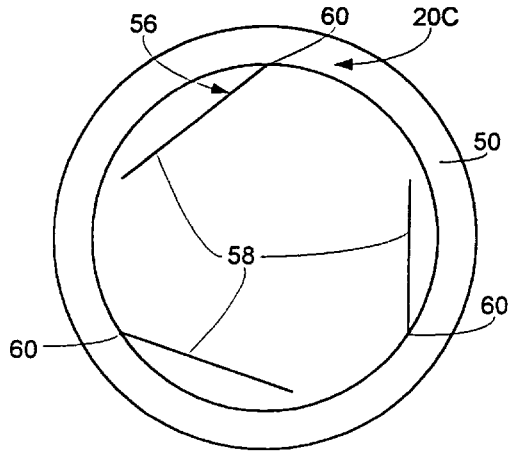
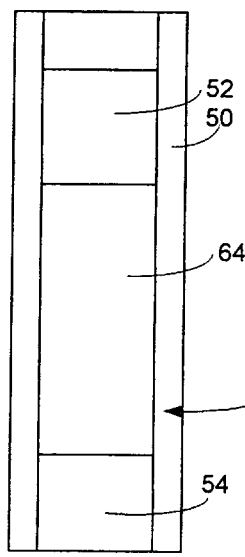
Fig. 9    Fig. 10

MINIMALLY INVASIVE SURGICAL INSTRUMENT FOR TISSUE IDENTIFICATION, DISLODGMENT AND RETRIEVAL AND METHODS OF USE

This application is a Continuation-In-Part of application Ser. No. 08/972,598, now U.S. Pat. No. 5,961,458, filed on Nov. 18, 1997, entitled "Minimally Invasive Surgical Probe For Tissue Identification And Retrieval And Method of Use", which is assigned to the same assignee as this invention, Care Wise Medical Products, Inc. of Morgan Hill, Calif. and whose disclosure is incorporated by reference herein.

BACKGROUND OF THE INVENTION

This invention relates generally to medical devices and methods of detection and treatment of cancer, and more particularly to minimally invasive medical systems including a radiation detecting probe for locating radioactively tagged tissue, e.g., a "sentinel" lymph node, within the body of the patient and for retrieving or removing that tissue.

The use of radioactive materials to tag tissue within a patient for effecting its localization and demarcation by radiation detecting devices has been disclosed in the medical literature for at least forty years. Significant developments in the localization and demarcation of tissue bearing radioactive isotope tags for diagnostic and/or therapeutic purposes have occurred since that time. In fact, it is now becoming an established modality in the diagnosis and/or treatment of certain diseases, e.g., cancer, to introduce monoclonal antibodies or other tumor or lymph node localizing agents tagged with a radioactive isotope (e.g., Technetium 99 m, Indium 111, Iodine 123, and Iodine 125) into the body of the patient. Such radiopharmaceuticals tend to localize in particular tissue, such as the cancerous tissue, so that the gamma radiation emitted by the isotope agent can be detected by a radiation detector, e.g., a probe. In particular, the radiation detector or probe is disposed or positioned adjacent portion of the patient's body where the cancerous tissue is suspected to be in order to detect if any radiation is emanating from that site. If it is this indicates that cancerous tissue is likely to be found at that site.

Prior art, hand-held, radiation detecting probes particularly suitable for such cancer-finding applications are commercially available from the assignee of this invention, Care Wise Medical Products, Inc., under the trademark C-TRAK. In U.S. Pat. Nos. 4,959,547 and 5,036,201 assigned to the same assignee as this invention there are disclosed hand-held radiation detecting probes having collimating means to establish the field of view or "solid angle of acceptance" of the probe. In U.S. Pat. Nos. 5,119,818 and 5,170,055, also assigned to the same assignee as this invention, there are disclosed hand-held radiation detecting probes and accessories optimized to biopsy radio-labeled tissues. In U.S. Pat. No. 4,801,803 (Donnan et al.) there is also disclosed a hand-held radiation detecting probe.

In the diagnosis and treatment of breast cancer and prostate cancer a radiopharmaceutical can be injected adjacent a detected tumor site, e.g., within the breast, to migrate to the closest draining lymph node (the "sentinel" node) so that localization of that node and its examination can be readily effected in order to evaluate the extent, if any, of metastasis of the cancer. Heretofore, no minimally invasive instrument, e.g., radioactivity detection probe, has existed to not only detect or localize the radioactively tagged tissue, e.g., the sentinel node, but also to safely dislodge it from adjacent tissue and to ensnare or trap it so that it can be removed for analysis.

It is a general object of this invention to provide a minimally invasive surgical instrument and method of use which addresses that need and which overcomes the disadvantages of the prior art.

SUMMARY OF THE INVENTION

These and other objects of the subject invention are achieved by providing a probe for minimally invasive introduction within the body of a living being. The probe is arranged to detect radiation emanating from radioactively tagged tissue, e.g., a sentinel lymph node, within the being's body to determine the location of that tissue. The probe is arranged to be readily manipulated and moved adjacent to the radioactively tagged tissue, and includes means (e.g., plural extendable members) for engaging (e.g., piercing or otherwise ensnaring) the radioactively tagged tissue to remove it from the being's body.

In accordance with another aspect of this invention the probe also preferably comprises a blunt tissue dissector. The tissue dissector is arranged to bluntly separate the radioactively tagged tissue from adjacent tissue so that the radioactively tagged tissue may be readily removed from the being's body.

In accordance with yet another aspect of the invention an attachment, e.g., a disposable sheath, for a radioactivity detecting probe is provided. The probe is a small device for minimally invasive introduction within the body of a living being to detect radiation emanating from radioactively tagged tissue, e.g., a sentinel lymph node, within the being's body to thereby determine the location of that tissue. The probe is arranged to be readily manipulated and moved adjacent to the radioactively tagged tissue. The attachment is arranged to be initially mounted on the probe prior to use and basically comprises means (e.g., plural extendable members) for engaging (e.g., piercing or otherwise ensnaring) the radioactively tagged tissue to remove it from the being's body.

In accordance with another aspect of this invention the attachment, e.g., sheath, also preferably comprises a blunt tissue dissecting device. The tissue dissecting device is arranged to bluntly separate the radioactively tagged tissue from adjacent tissue so that the radioactively tagged tissue may be readily removed from the being's body.

In accordance with another preferred aspect of this invention, the instrument may be fully integrated and self-powered, or may be partially integrated and self-powered.

In any case the instrument, probe and/or attachment for a probe may include means for illuminating the situs of the radioactively tagged tissue and may also include means for visualizing that situs.

DESCRIPTION OF THE DRAWING

Other objects and many attendant features of this invention will become readily appreciated as the same becomes better understood by reference to the following detailed description when considered in connection with the accompanying drawing wherein:

FIG. 6 is a longitudinal sectional view of a probe incorporating a single-hole collimator which can be used as part of the probe assembly of the subject invention;

FIG. 7 is a longitudinal sectional view of a probe incorporating a dividable single-hole collimator which can be used as part of the probe assembly of the subject invention;

FIG. 8 is an end view of the divided single-hole collimator shown in its undivided state;

FIG. 9 is an end view of the divided single-hole collimator shown in its divided state;

FIG. 10 is a longitudinal sectional view of a probe incorporating a back shielding light pipe which can be used as part of the probe assembly of the subject invention;

DETAILED DESCRIPTION OF THE PREFERRED EMBODIMENTS

Figure 1:
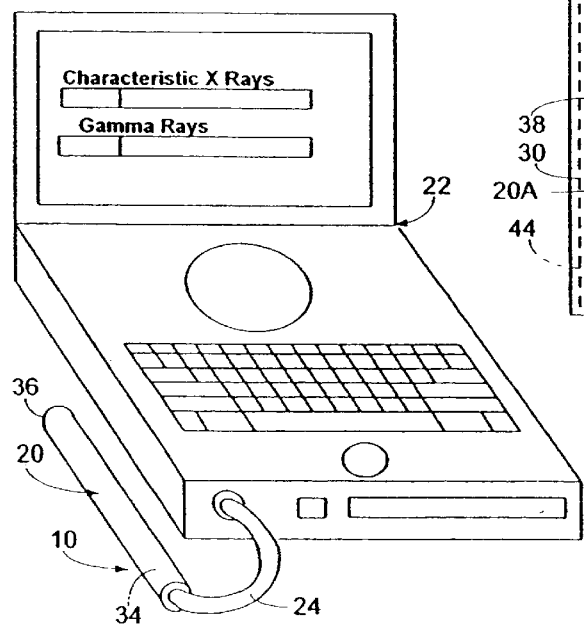
FIG. 1 is an isometric view of a system including the probe assembly of the subject invention.
Figure 11:
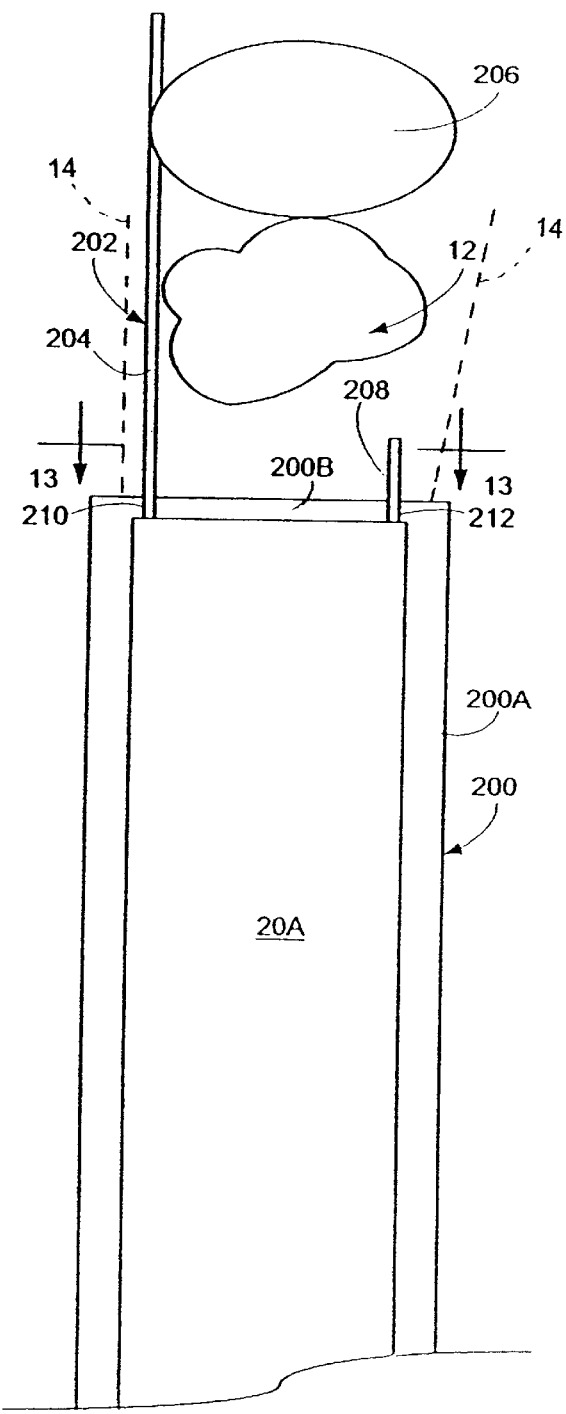
FIG. 11 is a longitudinal sectional view of another alternative embodiment of a sheath constructed in accordance with this invention and arranged for use with any suitable radiation detecting probe, which sheath is shown mounted on a conventional probe, and which includes a blunt dissection device and plural extendable members for entrapping radioactively tagged tissue, with the blunt dissection device being shown in the process of separating the radioactively tagged tissue, e.g., a radioactively tagged sentinel lymph node, from adjacent tissue.

Referring now to the drawing where like reference numerals refer to like parts there is shown at 10 in FIG. 1 a system incorporating a probe assembly 20 constructed in accordance with this invention. The system 10 is preferably constructed an arranged in accordance with the teachings of copending U.S. patent application, Ser. No. 08/430,589, filed on Apr. 25, 1995, entitled Apparatus and Methods For Determining Spatial Coordinates of Radiolabelled Tissue Using Gamma Rays And Associated Characteristic X-Rays, now U.S. Pat. No. 5,694,933, which is assigned to the same assignee as this invention and whose disclosure is incorporated by reference herein. The system is arranged to be used with any suitable radiopharmaceutical which is injected or otherwise introduced into the body of the being to be treated for specific uptake by the suspected cancer tissue or sentinel lymph node so that the probe assembly 20 of the system can determine the location of that cancer or lymph node and remove it with minimal invasion to the patient's body. To that end the system 10 basically comprises a minimal access surgical probe assembly 20 and an associated analyzer 22. The probe assembly is coupled to the analyzer by a cable 24 for detecting radiation emanating from the hidden source in a patient, e.g., a sentinel lymph node 12 (FIG. 2) tagged with the radiopharmaceutical, to localize that node, whereupon securement means (to be described later) in the probe can be operated to engage or otherwise ensnare the node so that it can be removed by the probe from the being's body for analysis.

Figures 2, 3:
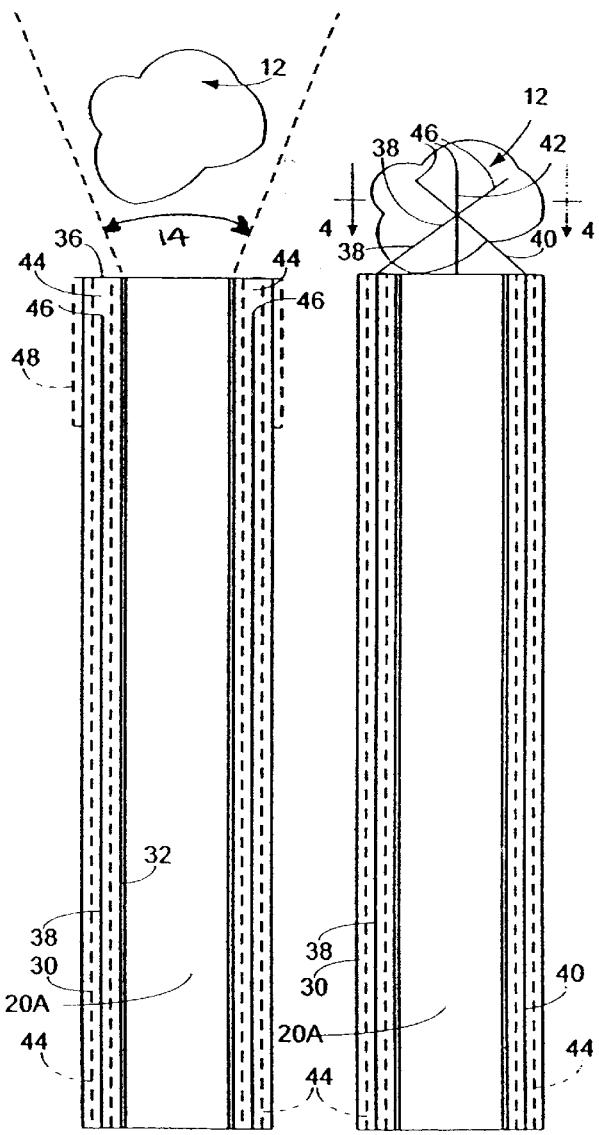
FIG. 2 is an enlarged longitudinal sectional view of one embodiment of the probe assembly of this invention shown located adjacent radioactively tagged tissue, e.g., a sentinel lymph node, to determine its location so that the probe assembly can be moved to a position wherein a portion of it is located immediately adjacent that tissue.
FIG. 3 is a view, similar to FIG. 2, but showing the probe assembly after it has be moved to a location immediately adjacent the tagged tissue and after its holding means has ensnared, e.g, pierced and trapped, that tissue.

The probe assembly 20 may be constructed so that it is an integrated instrument, e.g., the radiation detector and associated components and the securement means for ensnaring the node forming a single unit. Alternatively, and as shown in FIGS. 2 and 3 the probe assembly 20 may comprise a conventional radiation detecting probe 20A, like that described earlier, and a separate sheath or sleeve 30 for accommodating the probe 20A. To that end the sheath 30 has a central passageway 32 extending through it into which the probe 20A can be located. The sidewall of the sheath includes the heretofore mentioned tissue securement means. The sheath 30 may be constructed so that it is disposable, whereas the radiation detecting probe 20A is reusable. A detachable, side shield 48 in the form of a sleeve of radiation blocking material, may be located on the distal end of the probe assembly for use in high background radiation applications, e.g., when the sentinel node is close to the injection site.

In either case the probe assembly of this invention accomplishes its task by minimal invasive percutaneous penetration into the patient's body at the suspected situs of the lymph node, while the analyzer monitors the radiation picked up by the probe. By monitoring the radiation detected from the radiopharmaceutically-tagged tissue (e.g., gamma radiation, X radiation and/or annihilation radiation) and which is within the probe's solid angle of acceptance 14, the analyzer provides signals to the user to guide him/her so that the probe can be moved (by grasping its proximal end or handle 34) from the position of FIG. 2 to the position of FIG. 3 wherein its distal end 36 is located immediately adjacent the lymph node 12. At this point the tissue securement means (to be described hereafter) can be operated to ensnare the lymph node 12.

In the embodiment shown herein the securement means comprise three extendable, elongated piercing members or wires 38, 40, and 42. Each member is located within a longitudinally extending passageway 44 in the wall of the sheath 30. The members 38, 40, and 42 are arranged to be normally held in a retracted position within the sheath, so that their distal ends 46 are covered as shown in FIG. 2. This enables the probe assembly 20, i.e., the sheath 30 having the probe 20A therein, to be readily inserted either percutaneously or through a surgical incision to an internal situs, e.g., interstitial tissue, in which the distal end 36 of the probe assembly is located adjacent the radioactively tagged tissue 12, without interference caused by the extending members 38, 30 and 42. The probe can be moved or manipulated while the operator monitors the output of the analyzer 22 in order to locate the distal end of the assembly immediately adjacent the tagged tissue. At this time the extending members 38, 40 and 42 can be operated by means (not shown) to cause their distal ends 46 to extend out, e.g., 5–10 mm, of their respective passageways 44.

Figure 5:
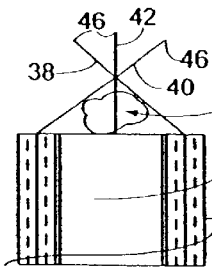
FIG. 5 is a view similar to FIG. 3, but showing only the distal end of the probe assembly, and wherein the tagged tissue, e.g., lymph node, is too small to be pierced by the holding means, but is nevertheless still snared or entrapped thereby.
Figure 4:
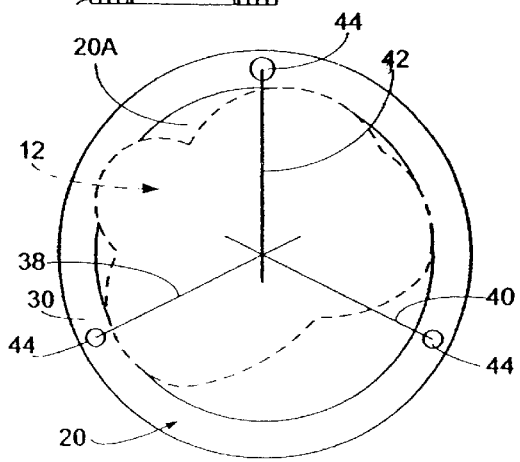
FIG. 4 is an enlarged sectional view taken along line 4—4 of FIG. 3.

In accordance with a preferred aspect of this invention the extendable members 38, 40 and 42 are arranged so that, when extended, their distal ends 46 extend inward at an acute angle, e.g., 30–60 degrees, to the central longitudinal axis of the probe assembly 20 and intersect each other as shown in FIGS. 3 and 4. This action causes the members 38, 40 and 42 to pierce into the tagged tissue, if the tagged tissue is sufficiently large (e.g., 3–4 mm or greater in diameter) and thereby "lock" it in place. If the tagged tissue is smaller, the intersecting extendable members 38, 40 and 42 will not pierce the tissue but will otherwise surround or "entrap" it, as shown in FIG. 5. In any case, the probe assembly 20 can then be retracted or withdrawn from the being's body, carrying the tagged tissue 12 with it.

In accordance with one aspect of this invention the sheath may include means to direct the distal ends 46 of the extending members 38, 40 and 42 at an acute angle inward, or those members may be formed so that they automatically assume that orientation when they are extended out of their respective passageways 44 in the sheath 30. Moreover, means (not shown) may be provided to adjust the angle at which the members 38, 40 and 42 extend outward from the sheath.

If additional means are deemed necessary to ensure that the tagged tissue 12 is either trapped between the extending members 38, 40 and 42 and the distal end 36 of the probe assembly 20 (as shown in FIG. 5), or is pierced and ensnared (as shown in FIGS. 3 and 4) so that it does not fall off of the probe assembly during the retrieval process, additional holding means (not shown) may be provided. That means may consist of a "purse string" coupled to the extending members 38, 40 and 42 to secure them together and to the ensnared tissue. Moreover, the extending members may include means, e.g., barbs, to ensure that the tissue once grabbed or pierced does not fall off. Such barbs may be annular or longitudinal or combinations of both.

The passageways 44 in the sheath can be used to provide various other functions for the probe assembly. For example suction, from means (not shown), can be used by the probe assembly 20 to aid in holding the tagged tissue 12 in place on the distal end 36 of the probe assembly 20. The suction means can also be used to remove blood or other fluid from the operative situs.

Energy application means, e.g., a unipolar or bipolar diathermy unit, may be provided to extend out of the sheath 30 in the probe assembly 20. For example, one of the wires 38, 40 or 42 can be a unipolar diathermy wire to be extended into the tagged tissue, if desired. If bipolar diathermy is desired, two of the wires 38, 40 or 42 may be used to provide it.

Any of the passageways 44 in the sheath 30 may be used to deliver any desired material, including biologically active materials, for any desired purpose. For example, any passageway 44 can be used to deliver some flowable material to the situs of the tagged tissue to prevent the migration of cells, e.g, cancer cells, therefrom or to kill such cells.

In order to expedite the tissue localization process the probe assembly may include collimation means, e.g., a snap-on collimator (not shown), an adjustable collimator, (not shown) etc., to establish or adjust the solid angle of acceptance 14 of radioactivity by the probe assembly 20.

While the system 10 may be used without an analyzer 22 constructed in accordance with the teachings of our aforementioned copending U.S. patent application Ser. No. 08/430,589, it is preferable to use such an analyzer. In this regard the analyzer can measure the characteristic x-ray photons and full energy gamma ray photons received by the probe's sensor to determine if the ratio of the characteristic x-ray photons to the full energy gamma ray photons is appropriate for the particular radiopharmaceutical used to tag the tissue, i.e., corresponds to the natural abundance of the characteristic x-rays and fill energy gamma rays for that radiopharmaceutical. If the ratio is appropriate that fact enables the operator to accurately determine the near field location of the radioactively tagged tumor since there could not be any far field source of radiation which could interfere with the precise location of the tumor (a source of far field radiation would result in an improper ratio of characteristic x-rays to full energy gamma rays). Conversely, an inappropriate ratio, e.g., a reading of significantly more full energy gamma-ray photons than characteristic x-ray photons, will indicate that the source of radiation is far field. Thus, the probe should be moved to a new position, until an appropriate ratio of characteristic x-ray photons to full energy gamma ray photons is detected.

As should be appreciated by those skilled in the art, the "sentinel node" procedure, which is the accepted modality of treatment for melanoma, and which will likely be the accepted modality of treatment for breast cancer can be effected percutaneously using the subject invention, instead of through conventional cut-down or open surgery, e.g., lumpectomy, as is the case at present. Moreover, the subject invention has particular utility for prostate cancer treatment, wherein the prostate containing the primary tumor is injected with a radiocolloid and any draining lymph nodes exhibiting radioactivity (sentinel lymph nodes) can be removed with minimum invasion to the patient. Similarly, lymph nodes identified by radiolabelled monoclonal antibodies and peptides can be detected and excised with minimum trauma.

The probe assembly 20 of this invention enables one to pierce and snare or to surround, apply suction to, suture or staple selected tagged tissue (e.g., a sentinel lymph node) and thus attach the tagged tissue to the probe tip in order to allow withdrawal of it as the probe is withdrawn. In the embodiment disclosed above the extending members or wires 38, 40 and 42 may be spring steel which are preformed to converge from a straight channel, alternatively they may be straight wires directed by angle channels, or other means in the sheath, or any combination thereof. The extending members may be tubular sections instead of solid wires (for reasons to be discussed later). In any case, the extending members can be adjusted during the operation to vary their angle of attack relative to the energy detecting probe's nose (distal end). A simple adjustment mechanism, such as a purse string attached to the tips of the extending elements can act against the intrinsic springiness or bias of the material making up those elements or can act against the applied force of the portion of the sheath causing the tips to be angled, in order to adjust the angle of attack. The angle can be adjusted from 30 to 60 degrees, in order to pierce and/or entrap and/or apply suction to the smallest lymph nodes. Additionally, at a given angle of attack, the tips of the three extending members can be advanced relative to the probe's tip to better accommodate very large lymph nodes or other tissue chunks. Moreover, at a given angle of attack, the tips of the three extending members can be retracted relative to the probe's tip to better accommodate very small lymph nodes, or other tissue chunks. Additionally, the probe 20A could be retracted relative to the sheath 30, and hence the tips of the extending members or wires 38, 40 and 42, to provide clearance for repositioning the angle of attack and so that they meet closer to the horizontal. As mentioned above, the extending members or wires can include barbs, like "fish hook barbs" and can be from about 0.1 to 3 mm long, designed to spread in response to tissue movement away from the probe's tip.

While the probe is shown with three extending members which are simultaneously advanced into or around the tissue in front of the probe tip the probe can make use of more or less members, as the case may be. In any case the probe can be used under external ultrasound guidance to accurately pierce, snare or surround, apply suction to the selected tagged tissue, while avoiding damage to adjacent blood vessels, nerves, peritoneum, pleura, and other important normal biological structures.

As mentioned earlier, it is also contemplated that the extending members, 38, 40 and 42, instead of being solid wires, can be hollow hypodermic tubing, capable of injecting appropriate substances into the lymph nodes or other tagged tissues to kill tumor cells, or to prevent the spread or seeding of tumor cells, or to initiate and propagate localized blood clotting, or for instilling other local/regional pharmacological agents. Moreover, extending members in the form of hollow tubes enable the application of suction therethrough as an additional attachment mechanism to the lymph node or other tagged tissue. Further still, the suction can be used to remove blood and/or excess fluids. As noted earlier, the channels or passageways 44 in which the extendable wires 38, 40 and 42 are located, can themselves serve as the channels for powerful suction attachment of the lymph node and other tissues. Moreover, these channels or passageways are suitable for injecting any appropriate substance into or around the lymph node or other tissues to kill tumor cells, or to prevent the spread or seeding of tumor cells, or to initiate and propagate localized blood clotting, or for instilling other local/regional pharmacological therapy, or for irrigation and suction of blood and or excess instilled fluids. Moreover, the passageways in which the extending solid wires are located, or the alternative embodiment of tubular wires, or both, can serve as means for installation of fluid solutions for other associated diagnostic and therapeutic purposes.

When the tagged node is ensnared by the probe assembly 20 it can be teased out of surrounding tissue by gentle pressure, under external ultrasound visualization, if desired. Thus, the minimally invasive radiation sensing tissue snaring probe of the invention is particularly suited to locate and retrieve sentinel nodes associated with any solid tumor, such as prostate, breast, lung, colon, rectal, and others. Scarring and trauma is thus minimized. Moreover, trauma-related-release of local growth factors, including platelet derived growth factors, which can lead to tumor reoccurrence, is also minimized.

The probe can be constructed so that it is any desired size. For example, it may be 5 to 16 mm in outside diameter, with a total length of about 9–18 inches (228.6 mm–457.2 mm). Specifically, it may be of an outside diameter of 9.5 mm for easy percutaneous introduction into the suspected site via a conventional 10 mm trocar. The distal end or nose of the probe may be configured to accept a snap on collimator, which may have approximately one millimeter channels bored into the walls, or cast as longitudinal channels or grooves on or within the inner wall of the snap on-collimator. The snap-on collimator may be made of Bismuth alloys or other low-toxicity, low-melting point, easily cast metals, or non-toxic radiation shielding composites, such as Barium filled epoxies.

An additional embodiment may consist of a 5 to 10 mm outside diameter straight probe 20A. An 8 mm version may be ensheathed in a closely fitting disposable plastic, sterile sheath 8.2 mm in inside diameter and 10 mm in outside diameter and including the tissue attachment means, i.e. the extending wires 38, 40 and 42. The optional outer sheathing cylinder 48 (FIG. 2) may be of 10.2 mm inside diameter and 12 mm outside diameter so it can be used to serve as an additional side shielding for the probe assembly 20 during the process of localizing or finding the tagged tissue or node. Alternatively, the sheathing cylinder 48 may be mounted on the probe 20A itself. Moreover, the sheath 48 may be slidable on whatever component it is mounted. The outer sheath 30, i.e., the portion which houses the extending wires 38, 40 and 42, can be made only about 25 mm long and may be constructed of any ionizing radiation shielding material. In use, that sheath may simply be slid back along the longitudinal axis of the probe 20A as the probe penetrates the skin and subcutaneous tissues. That sheath may also simply be slipped off the front of the probe 20A after percutaneous localization of the radioactive node or other tissue, prior to skin penetration. The outer sheath 30 should allow the probe to detect signal from the node as low as 2.5 per second, despite noise from the nearby injection site, which may be emitting as much as 37,000 counts per second. Positioning of the leading or distal edge 36 of the outer sheath 30 can be flush with the probe 20A tip or forward of the probe tip, as desired.

The radiation shielding necessary to initially find the node adjacent to a very high background count is substantially greater than the shielding required to track the dissection of that localized node. The sheath 30 or the optional outer sheath 48 may be about 10 half value layers thick (1.9 mm for Tungsten 95% alloy at 140 keV) and the intrinsic probe walls shielding may be about 7 half value layers thick (1.33 mm for Tungsten 95% alloy at 140 keV). Thus, the reusable probe sheath may be as little as 5 millimeters in diameter (2.66 mm thick with a wall, 2.0 mm diameter radiation detector) while still having 99% exclusion of side incident protons.

The detector may be a rod of Cesium Iodide or of Gadolinium Orthosilicate, either of which is only doped with a scintillation activator at one end to produce an active region approximately 3 mm long, in a rod that may be 100 mm long. In this arrangement, there is no light loss between the scintillation detector portion of the rod and the light pipe, as there were would if there were separate joined pieces of scintillator and light pipe. The sides and one end of the rod may be coated with reflective material, such as a thin-layer-deposition of gold, silver, platinum, etc., or a thin-layer-deposition of Teflon reflective material. Thus, a highly efficient, very small diameter intrastitial or endoscopic probe may be constructed, wherein the light pipe material provides backshielding against injection site radioactivity.

The diathermy capability of the probe assembly as described earlier provides the option of cutting attached tissues or of coagulating bleeding vessels. For unipolar or monopolar diathermy coagulation, only one of the extending wires is advanced from the probe tip and the probe is rotated. For bipolar diathermy, two wires are partially advanced, leaving a tissue gap between them. Monopolar diathermy can be accomplished with one or more wires, as desired.

A sterile disposable accessory (not shown) ensheathing the probe can be combined with a sterile disposable probe power cord, or can be combined with a sterile disposable power cord sheath. Alternatively, a self contained probe can be placed inside a "Ziploc" sterile disposable accessory container.

It is also contemplated that the probe itself can be self-contained, that is the probe includes any of the circuitry found in the entire system described heretofore, e.g., the radiation signal analyzing circuitry, and a self-contained power source, e.g., one or more batteries, for effecting tagged tissue localization and retrieval. Thus, the self-contained probe may include means operative in response to the signal analyzing circuitry for providing audible and/or visual signals of the type provided by the computer or any other signals suitable for perception by the personnel utilizing the probe. In the interest of compactness and simplicity, the self-contained probe may not include the means for producing the visual and/or audible signals, but may rather include some wireless transmission means, e.g., a radio frequency transmitter, an IR transmitter, a laser or other light transmitter, etc., for wirelessly transmitting signals from the probe to some receiver located outside the body of the patient, whereupon the visual and/or audible signals may be produced for perception by the operating personnel.

In FIG. 6 there is shown a probe incorporating a single-hole collimator which can be used as part of the probe assembly 20 of the subject invention. That probe is designated by the reference number 20B and basically comprises a cylindrical sidewall 50 formed of a radiation shielding material. A scintillation crystal 52 is located within the interior of the sidewall a short distance proximally of the distal end of the sidewall, so that the sidewall serves as a single hole collimator establishing the probe's solid angle of acceptance 14 for producing a valid signal. A photomultiplier or a photodiode 54 is located distally of the crystal 52 to receive the light flashes produced by the crystal 52 from radiation impinging on it within the probe's solid angle of acceptance.

Other collimation can be used to reduce or narrow the solid angle of acceptance of the probe of this invention. In fact, such collimation may be adjustable. To that end in FIGS. 7–9 there is shown a probe incorporating a dividable single-hole collimator which can be used as part of the probe assembly of the subject invention. That probe is designated by the reference number 20C and is identical in construction to probe 20B, except that it includes an operable collimation assembly 56 (to be described hereinafter). In the interests of brevity the common components of probes 20B and 20C will be given the same reference numbers and their construction and operation will not be reiterated. The operable collimation assembly 56 is arranged to be selectively operated in either a "single hole mode," shown in FIG. 9, or in a "divided hole mode," shown in FIGS. 7 and 8. In the single hole mode the probe 20C provides a field of view or solid angle of acceptance 14 similar to the probe 20B and which is shown in FIG. 6. In the divided hole mode, the probe 20C provides a narrower solid angle of acceptance 14 like that shown in FIG. 7. To accomplish that end the collimator assembly 56 is made up of plural, e.g., three, hinged pivotable wall members or septa 58. Each of the septa is a planar member made up of a radiation resistant material, e.g., lead, or tungsten or platinum-irridium, and which is hingedly connected at 60 to the inside surface of the cylindrical sleeve 50 immediately distally of the distal end of the scintillation crystal 52 to create two or more channels 62 (in the embodiment shown herein three such channels, to be described hereinafter, are formed as shown in FIG. 8).

When the probe 20C is in the single hole mode the septa 58 are pivoted back to the position shown in FIG. 9, whereupon virtually the entire interior space within the cylindrical sidewall 50 distally of the crystal 52 is available to have radiation pass therethrough within the solid angle of acceptance 14 shown in FIG. 6. In the divided hole mode the septa 58 are pivoted to the operative or closed position shown in FIG. 8 wherein each free edge (i.e., the edge opposite the edge which is pivotally connected to the cylindrical sidewall) engages the respective free edges of the other septa to effectively divide the interior of the cylinder distally of the crystal into three identically sized pie-shaped sectors or channels 62. Each of these channels forms what may be considered its own single hole collimator, so that the combined effect of these three "single hole collimators" is a combined (divided) collimator, whose combined solid angle of acceptance 14 is substantially narrower than when the probe 20C is in the single hole mode as can be seen in FIG. 7.

In FIG. 10 there is shown a probe 20D incorporating radiation back shielding component which can be used as part of the probe assembly of the subject invention. The probe 20D is similar to probe 20B described above, except for the inclusion of a backshielding lightpipe 64 (to be described hereinafter). In the interest of brevity the common features of probes 20B and 20D will be given the same reference numbers. The backshielding lightpipe 64 is formed of any suitable optically transparent but radiation resistant material, e.g., radiopaque, material. As is known, scintillation crystals typically require a dopant to scintillate in response to ionizing radiation. Undoped Gadolineum Orthosilicate or undoped Bismuth Germinate or undoped Cesium Iodide or even a lead-glass lightpipe can be used to form the backshielding lightpipe 64. Thus, with the probe 20D all scintillation events detected by the probe's crystal 52 will be those arising from the front (distal end) of the probe. Ideally the backshielding lightpipe 64 has the same optical index of refraction as the scintillation crystal 52. The simplest way to achieve this goal is to use an undoped light pipe that is made of the same material as the scintillation crystal, with an index of refraction matched optical coupling gel or adhesive (not shown). Alternatively, lead-glass can also be fabricated with various indices of refraction specifications to approximate the index of refraction of the scintillation crystal 52. An optical coupling compound with an index of refraction half way between the crystal and the lightpipe can be used to maximize optical performance of the two part assembly. An alternative, and more elegant approach, is to create a combined scintillator-lightpipe, starting with an undoped crystal lightpipe, that is without the dopant which allows the scintillation crystal to emit flashes of light. In particular, a rod of undoped scintillation crystal, such as undoped Gadolineum Orthosilicate or undoped Bismuth Germinate, or undoped Cesium Iodide is used, but only one end of the rod is doped with the necessary scintillation dopant to form a scintillation crystal at that end, while the undoped portion forms the lightpipe. As will be appreciated, this arrangement will not have an optical joint between the crystal and lightpipe. The deposition of dopants may be accomplished by any implantation technology appropriate to the crystal depth to be treated. Elimination of the optical joint should allow higher spectral resolution and higher sensitivity within the photopeak due to the elimination of optical interface losses.

Since lymph nodes are commonly found near blood vessels, damage to blood vessels is a significant potential complication of minimally invasive lymph node surgery. In accordance with one preferred embodiment of this invention the instrument probe or sheath for a probe may include a blunt dissecting device configured to create a dissection space in tissue planes which are adjacent tissue susceptible to damage upon physical removal of an immediately adjacent lymph node. Examples of such injury-susceptible tissue are large veins or a plexus of nerves. Thus, the incorporation of a blunt dissector into the invention can prove quite useful for minimizing trauma during sentinel node dissection. To that end, as will be described in detail later, the probe or the sheath for the probe preferably includes a blunt dissecting device, e.g., an inflatable balloon, for raising the lymph node off the surface of a large vein or a plexus of nerves to minimize possible injury to the vein/nerves during the node's extraction. The blunt dissecting device, whether a balloon or other suitable blunt dissecting component, can be used to gently separate the adjacent tissue planes to elevate the lymph node off of all nearby vessels or nerves. Moreover, as will also be discussed later, by using a balloon as the blunt dissection device and locating it at the tip of the probe or sheath wherein it is movable with respect thereto, the balloon can serve as additional means for retaining the lymph node onto the probe or sheath. In particular, the pressure applied by an inflated balloon can serve to hold the lymph node between it and the distal end of the probe or sheath to facilitate the removal of the lymph node by the instrument.

Turning now to FIGS. 11–15, there is shown a disposable sheath 200 constructed in accordance with this invention for releasable mounting on a probe 20A (like that described earlier or on any other suitable radiation detecting probe). The sheath is formed of any suitable material, e.g., plastic, and includes a circular sidewall portion 200A, flat distal end wall portion 200B, and a proximal wall portion (not shown). The hollow interior of the sheath is arranged to hold the radiation detecting probe 20A therein so that radiation within the probe's solid angle of acceptance 14 will be received through the distal portion of the sheath. The sheath includes a blunt dissection device 202, tagged tissue securement means in the form of plural extendable members 238, 240 and 242, and visualization means (to be described later). The blunt dissecting device can be of any suitable construction. In the exemplary embodiments shown herein it basically comprises an elongated extendable arm 204 on which an inflatable balloon 206 is mounted. The balloon can be formed of any suitable material, either elastic or inelastic. In any case the balloon is arranged to be inflated from a compact condition (not shown) wherein it lies flat against the arm 204 and located with a passageway 210 (to be described later) in the sidewall of the sheath 200 to an expended condition, like that shown in FIGS. 11 and 15. The inflation of the balloon is accomplished by introducing a fluid into it through a passageway (not shown) in the arm 204. The arm is an elongated linear member which is somewhat flexible to bend slightly in the interest of preventing damage to adjacent tissue when it is extended, yet is sufficiently rigid to hold the inflated balloon at a desired position to accomplish the gentle blunt dissection or separation of the lymph node from adjacent tissue. To that end, the arm has a thickness and resiliency of a conventional shirt collar stay, but is formed of a plastic material.

Figure 12:
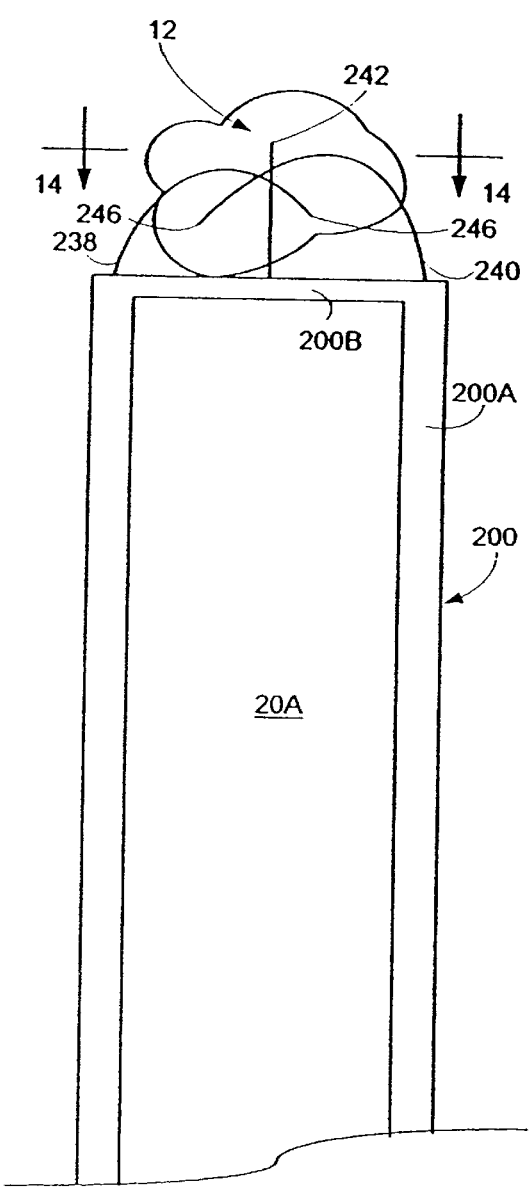
FIG. 12 is a view similar to FIG. 11, but showing the sheath in operation after its extendable members have been extended to entrap the radioactively tagged tissue so that the tagged tissue can be removed from the body of the patient.
Figure 13:
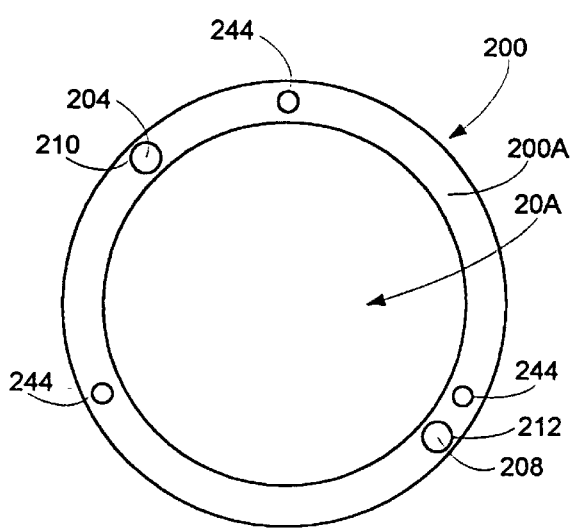
FIG. 13 is an enlarged sectional view taken along line 13—13 of FIG. 11.
Figure 14:
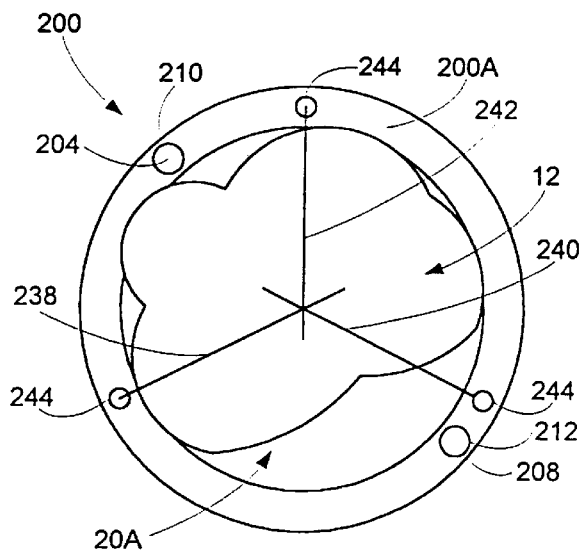
FIG. 14 is an enlarged sectional view taken along line 14—14 of FIG. 12.
Figure 15:
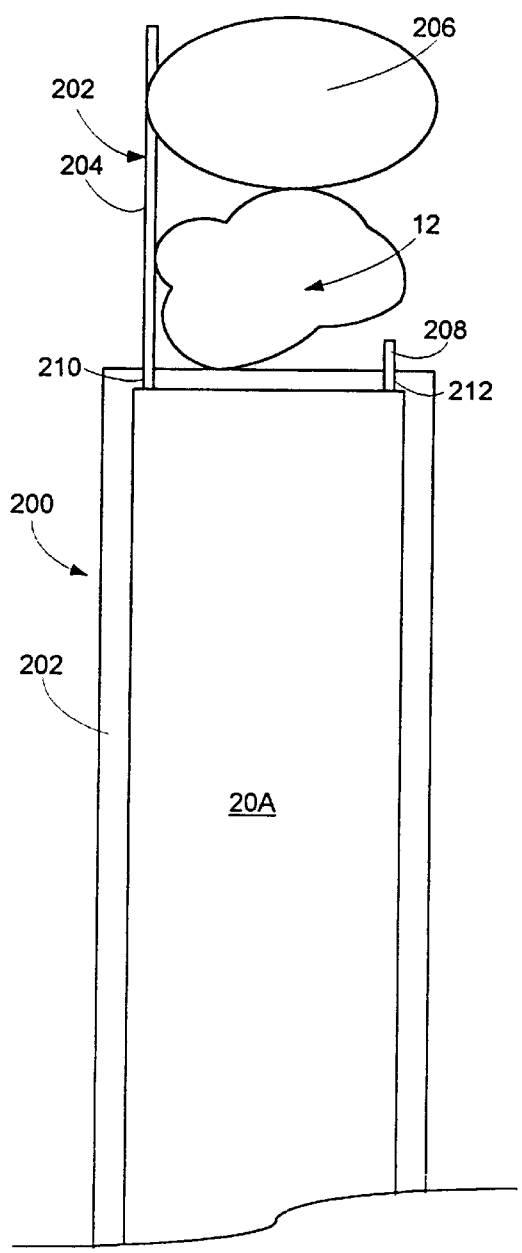
FIG. 15 is a view similar to FIG. 11, but showing the sheath with its blunt dissection device being used to entrap the radioactively tagged tissue, without necessitating use of the extendable members so that the tagged tissue can be removed from the body of the patient.

As mentioned above, the sheath 200 also includes plural extendable members 238, 240 and 242 which are used to releasably secure the tagged tissue, e.g., sentinel node 12, to the tip of the sheath so that it can be expeditiously removed from the patient's body. The details of the plural extendable members 238–242 will be described later. Suffice it for now to state that each of these members is a finger which is arranged to be extended out of a respective passageway 244 (FIGS. 13 and 14), whereupon its distal end portion assumes a curved configuration to entrap or ensnare the radioactively tagged tissue immediately adjacent the distal end of the sheath. It should be pointed out that the tagged tissue entrapment or ensnarement can be accomplished by one or more of the members piercing that tissue, such as shown in FIG. 12, or by the members extending around that tissue without piercing it.

The location of the tagged tissue to a position immediately adjacent the distal end of the sheath is accomplished in a similar manner as described above. In particular, the surgeon or other practitioner using the sheath 200 on the probe 20A must first locate or find the radioactively tagged tissue, e.g., a sentinel lymph node tagged with a radio-labeled monoclonal antibody or radio-labeled colloid. That is accomplished by use of the probe in the manner as described above or utilizing any other appropriate localizing technique. Once the probe has located the node, e.g., the node is immediately in front of the distal end of the probe, the fingers 238–242 can be extended in the same manner as described earlier with respect to fingers 38–42 of sheath 30 to either pierce the node or otherwise ensnare or entrap it. If the node is immediately adjacent some structure which is susceptible to injury by the node entrapment and removal procedure, e.g., if the node is laying right on top of a major vein or at the brachial plexus of nerves, then a different methodology will be utilized to remove that node from that described heretofore.

In particular, the alternative methodology entails the blunt dissection or separation of the tagged node from the adjacent tissue by means of the blunt dissecting device 202. For example, when the tagged node has been localized so that it is in front of and closely adjacent the tip of the sheath, the arm 204 with the uninflated balloon is then extended out of the passageway 210 and the balloon inflated. Once the balloon has been deployed (inflated) it can then be used to tease the node off of the adjacent tissue, e.g., the balloon can be inflated distally of the node and then dragged proximally to pull the node toward it as shown in FIG. 12. Thus, by appropriate inflation of the balloon and manipulation of the probe, the node can be gently nudged away from the adjacent tissue.

In some cases, as will be described later, the balloon can be positioned so that the separated node is entrapped between the balloon and the distal end of the probe, whereupon the removal of the probe effects the concomitant removal of the node. It is contemplated, however, that in most situations some degree of additional fixation or securement of the node to the probe will be desirable. To that end the extendable fingers 238–242 of the probe are operated, i.e., extended, so that they either pierce the node or surround the node as described earlier. If the blunt dissection is utilized to free the node from adjacent tissue and/or to capture it between the extended balloon and the distal end of the probe, the degree which the fingers will have to be extended from the probe to securely ensnare the node onto the probe may be significantly less than otherwise necessary without the use of the extended balloon. Thus, one of the features of this invention is that the use of the blunt dissector enables the separation of the node from the adjacent fragile tissue so that it can be nudged or otherwise moved to a safer location, whereupon the fingers can be extended for positively securing the node to the probe. Once that has been accomplished the node can be readily removed from the patient's body by merely withdrawing the probe.

As will be appreciated by those skilled in the art, the overwhelming majority of times, the sentinel lymph node is not so intimately attached to some tissue that one is worried about damage to adjacent tissue upon removal of the node. However, in some cases the adjacent tissue is quite susceptible to injury so blunt dissection will be very helpful.

As mentioned above, the sheath is preferably disposable so that after use on the probe it can be discarded. A new sheath can then be used on the probe to effect another tissue localization and removal procedure.

In accordance with a preferred aspect of this invention, the extendable arm 204 is preferably formed of a light-transmissive material so that when it is extended it can be used to carry light down its length to illuminate the operative situs. If desired, the balloon 206 can also be light-transmissive to further enhance the illumination of the operative situs. That situs can be visualized either directly (in the case where the sheath and probe are used in a cut-down surgical procedure) or indirectly via the sheath itself (in the case of where the sheath and probe are introduced via a small percutaneous incision or portal to the operative situs). To the latter end, the sheath 200 preferably includes a fiber optic bundle or single optic light pipe 208, such as has been employed heretofore in conjunction with surgical trocars to allow visualization of the tip of the sheath/probe combination. The light pipe 208 may include an angled light receiving distal end face (not shown) which is arranged to be extended out of a passageway 212 in the sheath's sidewall 200A and directed toward the operative situs, like shown in FIG. 11. Thus, light carried to the operative situs by the light-transmissive arm 204 can illuminate the area contiguous with the tip of the sheath so that an image of the tagged node and adjacent tissue can be carried back by the light pipe 208 to some means (not shown) either within the probe or outside of it, e.g., a video monitor, to visually display that situs to the surgeon. Visual inspection of the lymph node at the tip of the instrument is particularly valuable if a blue dye technique is used in conjunction with the radiopharmaceutical used to tag the tissue.

The material making up the balloon 206 may be either elastic or inelastic. In either case, the balloon is arranged to be inflated so that it can be extended outward from the arm a substantial distance, e.g., 10 mm. Moreover, the balloon is arranged to be either partially or fully inflated to achieve whatever amount of extension is desired for bluntly dissecting the tissue. This feature is a particular importance in order to ensure that tissue adjacent to the radioactively tagged tissue which may be susceptible to injury upon removal of the radioactively tagged tissue is protected from injury. For example, if the radioactively tagged tissue is a sentinel lymph node which is located immediately adjacent or on top of a vein or the brachial plexus of nerves, the blunt dissection device 202 can be utilized to gently lift the node off of the vein/nerves. Once the node is off the vein/nerves, the extendable members 238, 240, and 242 can be extended outward from their fully retracted position to an extended position like shown in FIG. 12 to entrap or ensnare the node in the same manner as described heretofore.

The sheath 200 may also include any of the features of the sheath 30 of the system 10 described earlier.

In FIGS. 16–19, there is shown an alternative embodiment of an instrument constructed in accordance with this invention. In particular, the instrument comprises a radiation detecting probe 300 constructed like probe 20A but also including a blunt dissecting device 302, plural extendable tissue-entrapping members 338–342, and visualization means like those described as part of the sheath 200 shown in FIGS. 11–15. To that end, the blunt dissector 302 is made up of an extendable arm 304 on which an inflatable balloon 306 is mounted. The arm 304 and balloon 306 are constructed and operate similarly to the arm 204 and the balloon 206. The tissue entrapping members 338–342 are also constructed and operate similarly to the fingers 238–242. The probe 300 also includes the light pipe 308, which is constructed and operates similarly to the light pipe 208.

Figures 16, 17, 18, 19:
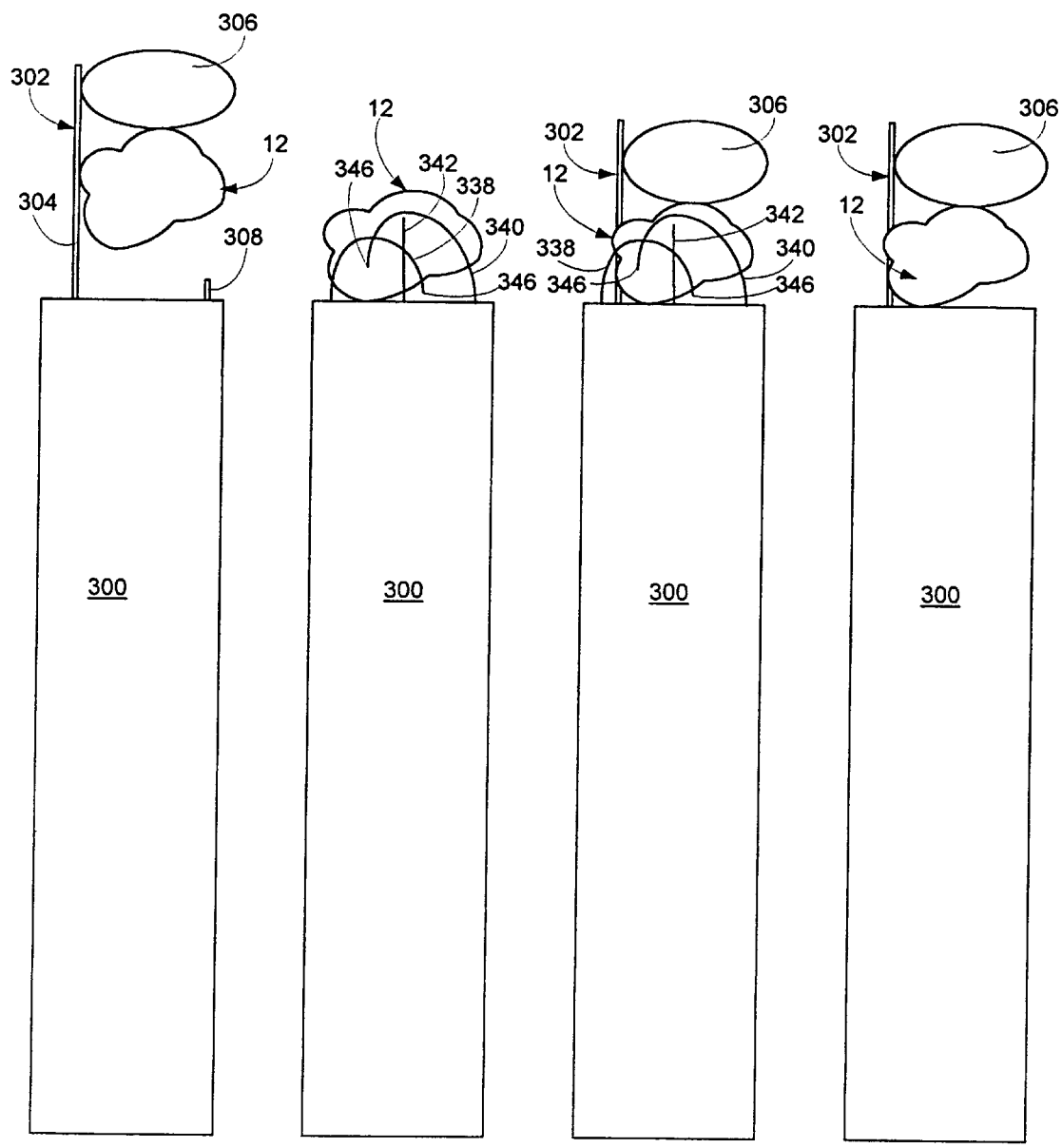
FIG. 16 is a side elevational view of an alternative embodiment of the instrument of this invention, namely, a radiation detecting probe having a blunt dissection device and plural extendable members, like those of the sheath of FIG. 11, built into the probe, shown during the process of bluntly dissecting the radioactively tagged tissue off of adjacent tissue.
FIG. 17 is a side elevational view like that of FIG. 16 but showing the probe's extendable members after they have entrapped the radioactively tagged tissue on the distal end of the probe to enable the tissue to be removed from the body of the patient.
FIG. 18 is a side elevational view also like that of FIG. 16 but showing the probe's blunt dissection device and its plural extendable members working in cooperation with each other to effect the entrapment of the radioactively tagged tissue to the probe so that the tissue can be removed from the body of the patient.
FIG. 19 is a side elevational view also like that of FIG. 16 but showing the use of the probe's blunt dissection device by itself to effect the entrapment of the radioactively tagged tissue to the probe so that the tissue can be removed from the body of the patient.

In FIG. 16, the probe 300 is shown after the tagged tissue, e.g., the sentinel lymph node, has been localized during the process of gently lifting it off of adjacent tissue (not shown) by means of its blunt dissecting device 302. In FIG. 17 the probe 300 is shown in the process of ensnaring (in this case, piercing) the freed tagged tissue (lymph node) to secure it to the distal end of the probe so that it can be removed from the patient's body. In FIG. 18 the probe 300 is shown with the blunt tissue dissection device and tissue ensnaring fingers working in conjunction to secure the freed tagged tissue (lymph node) to the distal end of the probe. In particular, the inflated balloon is retracted toward the probe tip to sandwich the node between it and the tip while the fingers are used to ensnare the node. This cooperation between the balloon and fingers provides enhanced securement of the tissue to the probe and may be indicated in some node removal procedures. Lastly, in FIG. 19 the probe 300 is shown with its blunt dissection device being used by itself to secure the node to the probe tip by merely retracting the inflated balloon to sandwich the node between it and the probe's tip.

Figure 20:
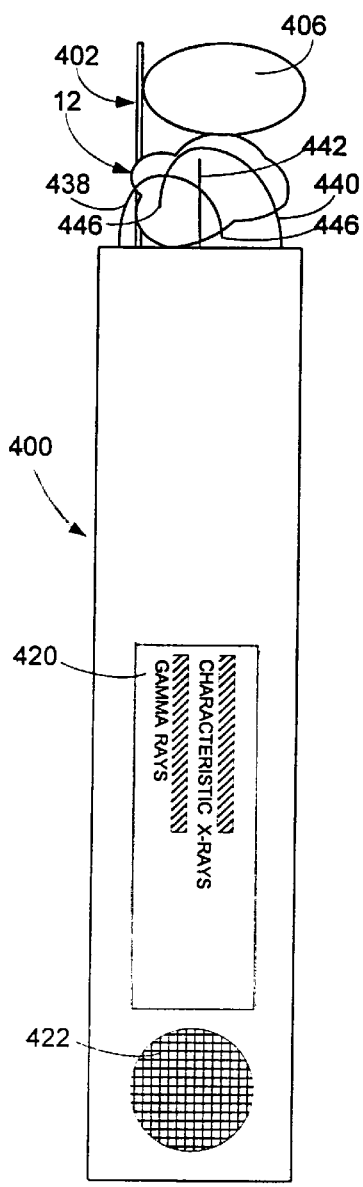
FIG. 20 is a side elevational view of yet another alternative embodiment of this invention, namely, a fully integrated radiation detection probe having a blunt dissecting device, plural extendable members and fully integrated electronics, power source, and signaling components.

In FIG. 20 there is shown another alternative embodiment of the subject invention. That embodiment consists of a fully integrated instrument 400, i.e., a probe incorporating all of the features of the system 10 plus a blunt dissector and extendable, tissue-ensnaring fingers, in a small, light-weight easily manipulatable unit. Thus, the instrument 400 basically comprises a probe having all of the electronics and electrical components (or their equivalents) found in the probe 20A and the analyzer 22 as well as the blunt dissecting device, tissue ensnaring members and visualization means of the embodiments of FIGS. 11–19. In particular, the instrument 400 includes a radiation detector and associated components (not shown), all of the signal processing and analyzer circuitry of the analyzer 22, all of the signaling circuitry, a visual (e.g., LCD) display 420, a sound generator or annunciator 422, and a self-contained power supply, e.g., a battery or battery pack (not shown). In addition the instrument 400 includes an extendable blunt dissection device 402 comprising an extendable arm 404 on which an inflatable balloon 406 is mounted. The arm 404 and balloon 406 are constructed and arranged to be operated in the same manner as described with respect to FIGS. 11–19. The probe 400 also includes three extendable members or fingers 438, 440, and 442, each having a curved distal end portion terminating in a free end 446. Each of the fingers is also constructed and arranged to be operated in the same manner as described above with reference to FIGS. 11–19.

As will be appreciated by those skilled in the art, the instrument 400 can be used by a surgeon or other medical practitioner to localize the radioactively tagged tissue by manipulating the probe at the operative situs while monitoring the signaling components, e.g., looking at the LCD display 420 and/or listening to the sounds produced by the annunciator 422. Once the tagged tissue has been localized, e.g., it is located immediately in front of the distal end of the probe, the blunt dissection device 402 and/or the extendable fingers 438, 440, and 442 can be used as described earlier to effect the securement and removal of the tagged tissue. To achieve good visualization of the procedure the arm for the balloon is transparent to carry light therethrough to illuminate the operative situs from a light source (not shown) within the instrument and powered by the instrument's internally located power supply (batteries).

Figure 21:
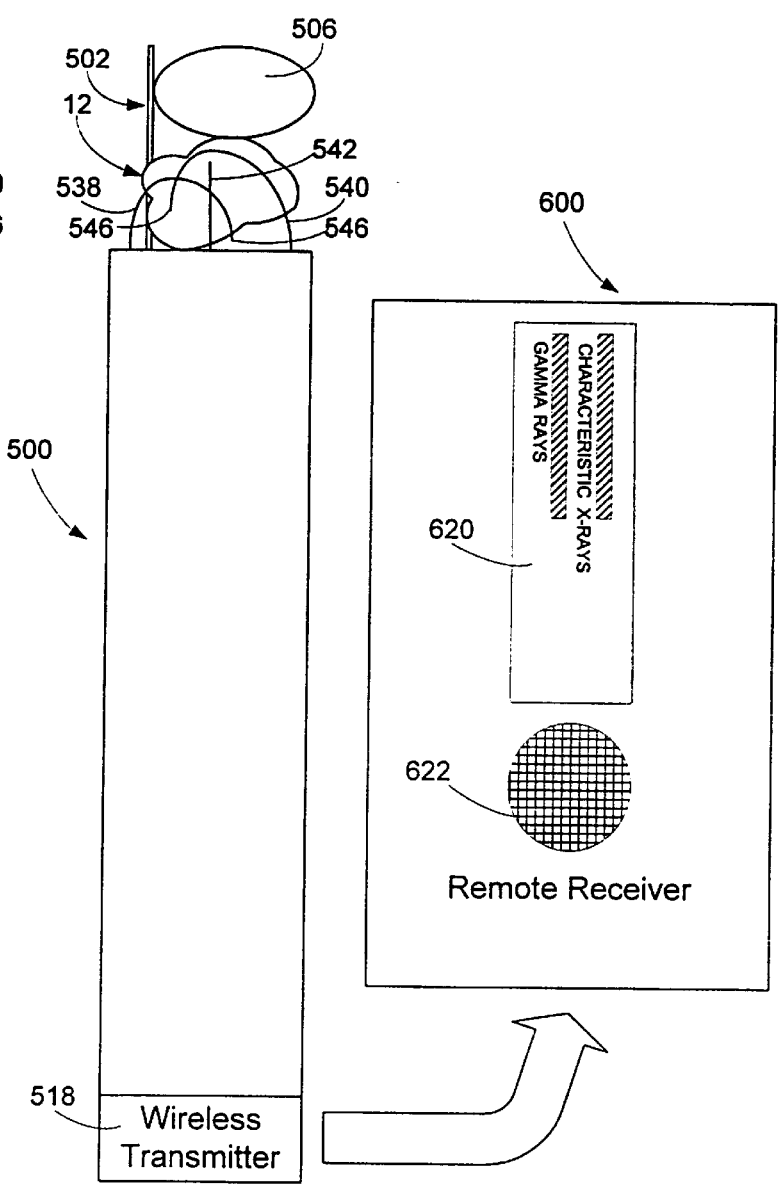
FIG. 21 is a side elevational view of still another alternative embodiment of this invention, namely, a partially integrated radiation detecting probe and an associated signaling, e.g., display/sound generating, unit.

In FIG. 21 there is shown another alternative embodiment of the subject invention. That embodiment consists of an integrated probe 500 incorporating all of the features of the instrument 400, except for the signaling components. Those signaling components are in the form of an externally located display/sound unit 600. In particular, the unit 600 includes a visual display 620 and associated circuitry and a sound generator or annunciator 622, each of which is constructed like the comparable components of the instrument 400 or of the system 10 described earlier, and a wireless receiver (not shown). The wireless receiver is arranged to receive wireless signals from the probe unit 500 so that the system conditions can be displayed on the visual display 620 for viewing by the surgeon or other medical practitioner using the system. The wireless receiver also provides signals to drive the annunciator 622 to provide audible signals to the surgeon. The wireless receiver can be of any suitable type, e.g., an infrared (IR) receiver, a radio-frequency (RF) receiver, a light or laser receiver, an ultrasonic receiver, etc. The wireless signals which are transmitted to the receiver are produced by a corresponding wireless transmitter 518 forming a portion of the probe unit 500. Thus, the electronic components within the probe 500 produce electrical signals representative of the operative conditions of the probe, and those signals are transmitted through the air from the probe to the remotely located unit 600 for production of the visual and audible signals required by the practitioner.

Like the fully integrated instrument 400, the probe unit 500 includes an extendable blunt dissection device 502 comprising an extendable arm 504 on which an inflatable balloon 506 is mounted (and which are constructed and arranged to be operated as discussed above with reference to FIGS. 11–19), and the three extendable fingers 538, 540, and 542 each having a curved distal end portion terminating in a free end 546. Each of the fingers is also constructed and arranged to be operated in the same manner as described above with reference to FIGS. 11–19.

The instrument 400 is used by a surgeon or other medical practitioner to localize the radioactively tagged tissue by manipulating the probe at the operative situs while monitoring the signaling components, e.g., looking at the LCD display 420 and/or listening to the sounds produced by the annunciator 422. Once the tagged tissue has been localized, e.g., it is located immediately in front of the distal end of the probe, the blunt dissection device 502 and/or the extendable fingers 53 8, 540, and 542 can be used as described earlier to effect the securement and removal of the tagged tissue. To achieve good visualization of the procedure the arm 504 for the balloon 506 is a transparent light carrying member to illuminate the operative situs in the same manner as described with reference to FIG. 20.

Even though the subject invention has been described for use in effecting the removal of cancerous tissue, it should be appreciated that the invention can be used to remove other tissue structures which have been tagged and located by the probe, and which are not cancerous. For example, various types of benign tumors or histologically benign fibrous nodular growths can also be located and removed from the body of the patient using the subject invention.

Moreover, it should be appreciated with the devices of the subject invention are to be used to localize and remove biological structures, which if penetrated or otherwise disturbed could result in the release of unwanted materials, e.g., cancer cells, the blunt dissector can be used alone or in combination with the extending fingers, but such fingers are extended so that they encircle or entrap the tagged tissue without piercing it. Piercing of the tagged tissue, e.g., a tumor, may be acceptable in various cases, e.g., a patient having systemic metastatic cancer wherein removal of the tumor is desired for the palliative reasons, such as debulking.

Instruments constructed in accordance with the subject invention may incorporate a blunt dissector in the probe or in the sheath arranged to be attached to the probe, with or without the extendable members to ensnare the tagged tissue. Similarly, instruments constructed in accordance with the subject invention may incorporate extendable members in the probe or in the sheath arranged to be attached to the probe to ensnare the tagged tissue, with or without the blunt dissector to effect separation of the tagged tissue from adjacent tissue along a tissue plane. Further still, the extending members can be arranged so that they can merely encircle or "cage in" the tagged tissue or can pierce that tissue. In either case the tagged tissue is entrapped or ensnared on the instrument so that it can be removed from the body of the patient by retracting the instrument.

The use of a blunt dissection device as part of the probe or as part of a sheath for use on a probe provides a further advantage to the medical practitioner over the ability to facilitate the removal of the tagged tissue. In this regard the use of an inflatable balloon blunt dissecting device gives the practitioner the ability to assist or expedite hemostasis at the situs from which the tagged tissue has been removed. In particular, after removal of the tagged tissue by the instrument of this invention, the instrument can be reinserted to the operative situs at which time the arm carrying the inflatable balloon can be extended to position the balloon at the desired position at the operative situs, then the balloon can be inflated and held in place for a few minutes or more to close off adjacent capillaries or other blood vessels to thereby promote hemostasis. For some hemostasis-inducing applications, the balloon may be constructed so that it is capable of greater expansion, e.g., 15 mm, than used for the blunt dissection operation. Thus for those applications, the balloon may be formed of an elastic material, such as nitrile rubber.

While the embodiments of the invention shown in the drawing and discussed above include a single blunt dissection device, i.e., a single extendable finger having an inflatable balloon mounted thereon, such a construction is merely exemplary. Thus, instruments constructed in accordance with this invention can make use of plural blunt dissection devices and such devices may be operated independently of one another or in coordination. In a similar manner even though the embodiments of the invention shown in the drawing and discussed above include three extendable members, e.g., curved or straight fingers, to ensnare the tagged tissue, such a construction is also merely exemplary. Thus, instruments constructed in accordance with this invention can make use of a single or any number of extendable members to ensnare the tagged tissue. If plural members are used they may be operated independently of one another or in coordination.

While the extendable fingers may be either straight (e.g., linear) or curved, for most applications curved fingers are preferable. In this regard, by having the free end of the extendable fingers curve toward the distal end of the probe, the chance of unintentional penetration of adjacent tissue is reduced. To further this goal, it is also preferred that the radius of curvature of the portion of each finger contiguous with its free end is less than the one half of the diameter of the distal end of the probe so that the free end of each finger will not extend outward laterally from the distal end of the probe where it could pose a puncture hazard to adjacent tissue (i.e., the free end of each finger will be located within the bounds of the periphery of the distal end of the probe and closely adjacent the end surface of the probe or sheath, as the case may be. Moreover, it is desirable to have each extendable member have a different radius of curvature, with one finger's radius of curvature being such that the free end thereof is located immediately adjacent the central longitudinal axis of the probe, and with the other fingers' respective radii of curvature being slightly smaller and slightly greater, e.g., 1 or 2 mm smaller or larger. This feature ensures that when it is desired to pierce the tagged tissue (e.g., the node) at least one of the fingers will pierce the center of it, while the others pierce it on either side, thereby effectively securing it to the probe. With this arrangement the effective piercing and securement of lymph nodes ranging from 1 mm to 15 mm in size is anticipated.

The fingers may be solid or hollow to utilize the features as discussed earlier with respect to fingers 38, 40 and 42.

The use of a light transmissive arm for the inflatable balloon of the blunt dissection device while not mandatory is nevertheless desirable since it provides a convenient means for effecting the illumination of the operative situs. Thus, the blunt dissection device may not incorporate any means for illuminating the operative situs. Such illumination means may be provided by some other component or structure forming a portion of the instrument, alternatively no illumination means may be utilized as part of the probe or sheath. So too, the instrument need not include any light receptor, e.g., a fiber optic bundle, light pipe, or any other pick-up device for receiving an image of the operative situs, to enable indirect visualization of the operative situs (i.e., visualization via the instrument.

Since the probes or sheaths for use on probes which constitute the subject invention can be made to be of small diameter, e.g., 5 mm to 10 mm in diameter, they are particularly suitable for use via a small percutaneous portal or opening in the patient to localize and then remove the tagged tissue, thereby accomplishing the advantages of "minimally invasive surgery." Alternatively, they can be used during a conventional "cut-down" type of surgical procedure. For the latter type of applications it should be evident that the probes, sheaths or other instruments of this invention can be somewhat bigger in size, but still sufficiently compact and light weight to enable facile manipulation by the surgeon or other medical practitioner.

Without further elaboration the foregoing will so fully illustrate our invention that others may, by applying current or future knowledge, adopt the same for use under various conditions of service.

What is claimed is:

1. An instrument for minimally invasive introduction within the body of a living being including a probe and a blunt tissue dissector, said probe including a radiation detector for detecting radiation emanating from radioactively tagged tissue within the being's body to determine the location of the radioactively tagged tissue to enable the instrument to be moved adjacent to the radioactively tagged tissue, said tissue dissector being arranged to bluntly separate the radioactively tagged tissue from adjacent tissue so that the radioactively tagged tissue may be readily removed from the being's body.

2. The instrument of claim 1 wherein said blunt tissue dissector includes an inflatable balloon.

3. The instrument of claim 2 wherein said instrument includes a grabbing member for grabbing the radioactively tagged tissue.

4. The instrument of claim 3 wherein said grabbing member includes at least one extendable member to ensnare the radioactively tagged tissue.

5. The instrument of claim 4 wherein said at least one extendable member is arranged to pierce into the radioactively tagged tissue.

6. The instrument of claim 3 wherein said grabbing member includes plural extendable members to engage the radioactively tagged tissue from plural directions to ensnare it.

7. The instrument of claim 3 wherein said probe comprises a body member formed of a radiation blocking material and having radiation detecting means located within said body member, said body member having a distal end portion and a proximal end portion, said proximal end portion being arranged to be held in the hand of a user, said distal end portion being arranged to be directed toward a suspected location of the radioactively tagged tissue.

8. The instrument of claim 7 wherein said blunt tissue dissector is located at said distal end portion of said body member.

9. The instrument of claim 2 wherein said probe comprises a body member having a distal end portion and a proximal end portion, said proximal end portion being arranged to be held in the hand of a user, said distal end portion being arranged to be directed toward a suspected location of the radioactively tagged tissue, said balloon being extendable from said distal end portion to an extended position and being retractable from said extended position towards said distal end portion to ensnare the radioactively tagged tissue between it and said distal end portion, thereby enabling said instrument to remove the radioactively tagged tissue from the body of the being.

10. The instrument of claim 9 wherein said balloon is mounted on an arm, said arm being coupled to said probe and being arranged to be extended from said distal end portion and retracted towards said distal end portion to carry said balloon to the position ensnaring the radioactively tagged tissue between said balloon and said distal end portion of said probe.

11. The instrument of claim 10 wherein said balloon is arranged to be inflated when said balloon is in said extended position.

12. The instrument of claim 1 wherein said instrument includes a grabbing member for grabbing the radioactively tagged tissue.

13. The instrument of claim 12 wherein said grabbing member includes at least one extendable member to ensnare the radioactively tagged tissue.

14. The instrument of claim 13 wherein said at least one extendable member is arranged to pierce into the radioactively tagged tissue.

15. The instrument of claim 13 wherein said probe comprises a body member having a distal end portion and a proximal end portion, said proximal end portion being arranged to be held in the hand of a user, said distal end portion being arranged to be directed toward a suspected location of the radioactively tagged tissue, and wherein said extendable member is arranged to be extended outward from said distal end of said probe, said extendable member including a portion curving backward toward said distal end of said probe.

16. The instrument of claim 15 wherein said instrument includes plural extendable members, each of which being arranged to be extended outward from said distal end of said probe, each of said extendable members including a portion curving backward toward said distal end of said probe.

17. The instrument of claim 12 wherein said grabbing member includes plural extendable members to engage the radioactively tagged tissue from plural directions to ensnare it.

18. The instrument of claim 17 wherein said probe includes a distal end portion and each of said extendable members includes a free end arranged to be extended from said distal end portion of said probe, and when so extended each of said members assumes an arcuate configuration so that its free end is located closely adjacent said distal end portion of said probe.

19. The instrument of claim 18 wherein said probe is an elongated member of small diameter arranged to be readily held on the hand, and wherein the radius of curvature of at least one of said extendable members is approximately equal to one-half of the diameter of the probe.

20. The instrument of claim 12 wherein said probe comprises a body member formed of a radiation blocking material and having radiation detecting means located within said body member, said body member having a distal end portion and a proximal end portion, said proximal end portion being arranged to be held in the hand of a user, said distal end portion being arranged to be directed toward a suspected location of the radioactively tagged tissue.

21. The instrument of claim 20 wherein said blunt tissue dissector is located at said distal end portion of said body member.

22. The instrument of claim 1 wherein said blunt tissue dissector is arranged to separate the radioactively tagged tissue from adjacent tissue along a tissue plane interface.

23. The instrument of claim 1 wherein said instrument is arranged to provide an output signal in response to the radiation detected thereby.

24. The instrument of claim 23 wherein said output signal varies based on the placement of said instrument with respect to said radioactively tagged tissue.

25. The instrument of claim 24 wherein said output signal that varies based on the placement of said instrument is in a form that is perceptible by a user of the system.

26. The instrument of claim 25 wherein said blunt tissue dissector includes an inflatable balloon.

27. The instrument of claim 1 wherein said blunt tissue dissector is arranged to carry illumination through at least a portion of it to illuminate the radioactively tagged tissue.

28. The instrument of claim 1 wherein said blunt tissue dissector is arranged to be releasably secured to said probe.

29. The instrument of claim 28 additionally comprising a grabbing member for grabbing the radioactively tagged tissue.

30. The instrument of claim 29 wherein said grabbing member is arranged to be releasably secured to said probe.

31. The instrument of claim 1 wherein said probe comprises a small diameter elongated member arranged to be readily held in the hand.

32. The instrument of claim 31 wherein said blunt tissue dissector is arranged to be releasably secured to said probe.

33. The instrument of claim 32 additionally comprising a grabbing member for grabbing the radioactively tagged tissue.

34. The instrument of claim 31 wherein said grabbing member is arranged to be releasably secured to said probe.

35. The instrument of claim 34 wherein said blunt tissue dissector and said grabbing member are combined as an integral unit arranged to be releasably mounted on said probe.

36. The instrument of claim 34 wherein said blunt tissue dissector, said grabbing member and said probe are combined as an integral unit.

37. The instrument of claim 1 additionally comprising a fluid introduction passage for providing a fluid through said instrument into the body of the being.

38. The instrument of claim 1 additionally comprising a fluid extraction passage for removing fluid from the body of the being through said instrument.

39. The instrument of claim 37 additionally comprising a fluid extraction passage for removing fluid from the body of the being through said instrument.

40. The instrument of claim 39 wherein said blunt tissue dissector is arranged to be releasably secured to said probe.

41. The instrument of claim 40 additionally comprising a grabbing member for grabbing the radioactively tagged tissue.

42. The instrument of claim 41 wherein said grabbing member is arranged to be releasably secured to said probe.

43. The instrument of claim 42 wherein said probe comprises a small diameter elongated member arranged to be readily held in the hand.

44. The instrument of claim 43 wherein said blunt tissue dissector, said grabbing member, said fluid introduction passageway, and said fluid extraction passageway are combined as an integral unit arranged to be releasably mounted on said probe.

45. The instrument of claim 44 wherein said integral unit comprises a disposable member.

46. The instrument of claim 45 wherein said disposable member comprises a sleeve arranged to be mounted on said probe.

47. A method of removing radioactively tagged tissue within a living being's body, said method comprising the steps of:

(1) providing an instrument including a probe and a tissue dissector for minimally invasive introduction within the body of the being, said probe being arranged for detecting radiation emanating from radioactively tagged tissue within the being's body and for providing signals indicative thereof, (2) positioning said probe so that a predetermined portion of said probe is located adjacent the radioactively tagged tissue in response to said signals, (3) operating said tissue dissector to bluntly separate the radioactively tagged tissue from adjacent tissue, and (4) removing the radioactively tagged tissue from the being's body.

48. The method of claim 47 wherein said tissue dissector includes an inflatable balloon, and wherein said method comprises inflating said balloon to effect the separation of said radioactively tagged tissue.

49. The method of claim 47 wherein said instrument includes a grabbing member for grabbing the radioactively tagged tissue radioactively tagged tissue and wherein said method comprises operating said grabbing member to grab the radioactively tagged tissue for removing said radioactively tagged tissue from the body of the being.

50. The method of claim 47 wherein said blunt dissector is arranged to engage tissue at the interface of said radioactively tagged tissue and adjacent tissue to separate the radioactively tagged tissue therefrom.

51. The method of claim 47 wherein said method of removing radioactively tagged tissue is a method of removing radioactively tagged tissue that comprises a tumor.

52. The method of claim 47 wherein said method of removing radioactively tagged tissue is a method of removing radioactively tagged tissue that comprises a lymph node.

53. The method of claim 52 wherein said method of removing radioactively tagged tissue is a method of removing a lymph node that is a sentinel node.

54. The method of claim 53 wherein the step including providing a probe having an output signal includes providing a probe having an output signal that is visible.

55. The method of claim 47 wherein said step of providing an instrument including a probe includes providing a probe having an output signal indicative of the radiation detected thereby, and wherein said method comprises guiding the positioning of said instrument in response to said output signal.

56. The method of claim 55 wherein said step including providing a probe having an output signal includes providing a probe having an output signal that is perceptible by a user of the system to effect the positioning of said instrument in response thereto.

57. The method of claim 56 wherein the step including providing a probe having an output signal includes providing a probe having an output signal that is audible.

58. The method of claim 47 additionally comprising illuminating said radioactively tagged tissue via said instrument.

59. The method of claim 47 additionally comprising introducing a fluid adjacent said radioactively tagged tissue via said instrument.

60. The method of claim 47 additionally comprising extracting a fluid from a location adjacent said radioactively tagged tissue.

61. The method of claim 60 additionally comprising introducing a fluid adjacent said radioactively tagged tissue via said instrument.

62. The method of claim 47 additionally comprising the step of providing an inflatable member via said instrument to cause hemostasis at the situs of the radioactively tagged tissue after it has been removed.

* * * * *